US009616400B2

(12) United States Patent
Rahm et al.

(10) Patent No.: US 9,616,400 B2
(45) Date of Patent: Apr. 11, 2017

(54) DRIVING DEVICE OF A METERING AND MIXING APPARATUS

(71) Applicant: SIKA TECHNOLOGY AG, Baar (CH)

(72) Inventors: Markus Rahm, Volketswil (CH); Christian Schultheiss, Pfäffikon (CH); Walter Fäh, Volketswil (CH); Pascal Tanner, Schmerikon (CH)

(73) Assignee: SIKA TECHNOLOGY AG, Baar (CH)

( * ) Notice: Subject to any disclaimer, the term of this patent is extended or adjusted under 35 U.S.C. 154(b) by 259 days.

(21) Appl. No.: 14/311,845

(22) Filed: Jun. 23, 2014

(65) Prior Publication Data
US 2014/0301156 A1  Oct. 9, 2014

Related U.S. Application Data

(63) Continuation of application No. PCT/EP2012/075155, filed on Dec. 12, 2012.

(30) Foreign Application Priority Data

Dec. 21, 2011  (EP) .................................... 11194942

(51) Int. Cl.
*B01F 15/02* (2006.01)
*B05C 17/005* (2006.01)
(Continued)

(52) U.S. Cl.
CPC .......... *B01F 15/0278* (2013.01); *A61C 5/064* (2013.01); *B01F 13/0023* (2013.01);
(Continued)

(58) Field of Classification Search
CPC ................................................ B01F 15/0237
(Continued)

(56) References Cited

U.S. PATENT DOCUMENTS 5,020,693 A * 6/1991 Ernst .................... B05C 17/015
                                                    222/137
5,605,252 A * 2/1997 Owen .................... B01F 15/04
                                                    222/1
(Continued)

FOREIGN PATENT DOCUMENTS

DE         32 33 366 A1    9/1983
EP         0 057 465 A2    8/1982
(Continued)

OTHER PUBLICATIONS

Notification of Transmittal of Translation of the International Preliminary Report on Patentability (Form PCT/IB/338 and PCT/IB/373) and the Written Opinion of the International Searching Authority (Form PCT/ISA/237) issued on Jul. 3, 2014, by the International Bureau of WIPO for International Application No. PCT/EP2012/075155. (9 pages).

(Continued)

*Primary Examiner* — David Sorkin
(74) *Attorney, Agent, or Firm* — Buchanan Ingersoll & Rooney PC

(57) ABSTRACT

A driving device of a metering and mixing apparatus for multi-component substances is disclosed, which driving device can have at least two cartridge holders for holding interchangeable cartridges with individual substance components, a discharging apparatus for simultaneously discharging the substance components from the cartridges through component outlets with the aid of discharging pistons entering the cartridge holder or cartridges, and a mixing apparatus which is connected to the component outlets, for mixing the discharged substance components and discharging the latter in mixed form, and a transmission unit for the connection of a drive motor, wherein the transmission unit can have a detector for detecting at least one counter pressure which builds up during the discharging (Continued)

of at least one of the substance components, and a controller, which is connected on an inlet side to the detector for bringing about a driving control function in response to a detection result.

19 Claims, 6 Drawing Sheets

(51) Int. Cl.
*A61C 5/06* (2006.01)
*B01F 13/00* (2006.01)
*B01F 15/04* (2006.01)
*B05C 17/01* (2006.01)

(52) U.S. Cl.
CPC ........ *B01F 15/0237* (2013.01); *B01F 15/042* (2013.01); *B05C 17/00553* (2013.01); *B05C 17/00566* (2013.01); *B05C 17/00576* (2013.01); *B05C 17/00596* (2013.01); *B05C 17/0103* (2013.01); *B05C 17/014* (2013.01); *B01F 2215/0027* (2013.01); *B01F 2215/0039* (2013.01); *B05C 17/0116* (2013.01); *B05C 17/0133* (2013.01)

(58) Field of Classification Search
USPC ................ 366/151.1, 152.1, 162.3, 184, 190
See application file for complete search history.

(56) References Cited

U.S. PATENT DOCUMENTS

| | | | |
|---|---|---|---|
| 6,315,164 B1 * | 11/2001 | Muhlbauer | A61C 5/064 222/325 |
| 2003/0022128 A1 | 1/2003 | Heymann et al. | |
| 2008/0144426 A1 | 6/2008 | Janssen et al. | |
| 2009/0039113 A1 | 2/2009 | Hsu et al. | |
| 2012/0148980 A1 | 6/2012 | Gramann et al. | |
| 2013/0277390 A1 | 10/2013 | Buck et al. | |
| 2014/0092704 A1 | 4/2014 | Janssen et al. | |

FOREIGN PATENT DOCUMENTS

| | | |
|---|---|---|
| EP | 1 279 379 A1 | 1/2003 |
| EP | 2 468 415 A1 | 6/2012 |
| WO | WO 2008/076941 A1 | 6/2008 |
| WO | WO 2011/025831 A1 | 3/2011 |

OTHER PUBLICATIONS

International Search Report (PCT/ISA/210) mailed on Jan. 24, 2013, by the European Patent Office as the International Searching Authority for International Application No. PCT/EP2012/075155.
Written Opinion (PCT/ISA/237) mailed on Jan. 24, 2013, by the European Patent Office as the International Searching Authority for International Application No. PCT/EP2012/075155.
International Search Report (PCT/ISA/210) mailed on Feb. 5, 2013, by the European Patent Office as the International Searching Authority for International Application No. PCT/EP2012/076508.
Written Opinion (PCT/ISA/237) mailed on Feb. 5, 2013, by the European Patent Office as the International Searching Authority for International Application No. PCT/EP2012/076508.
International Search Report (PCT/ISA/210) mailed on Feb. 5, 2013, by the European Patent Office as the International Searching Authority for International Application No. PCT/EP2012/075192.
Written Opinion (PCT/ISA/237) mailed on Feb. 5, 2013, by the European Patent Office as the International Searching Authority for International Application No. PCT/EP2012/075192.
Chinese Office Action issued in corresponding Chinese Patent Application No. 2014-547848 dated Oct. 4, 2016.

* cited by examiner

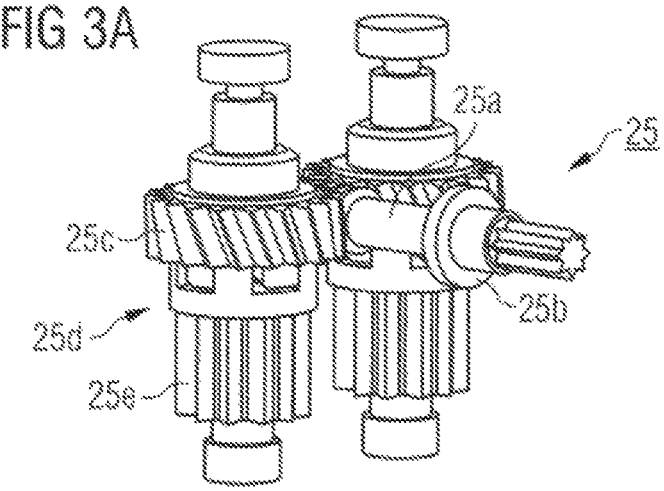
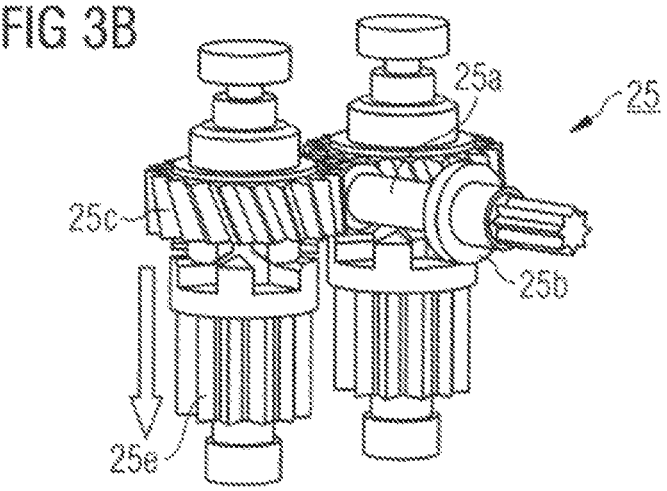
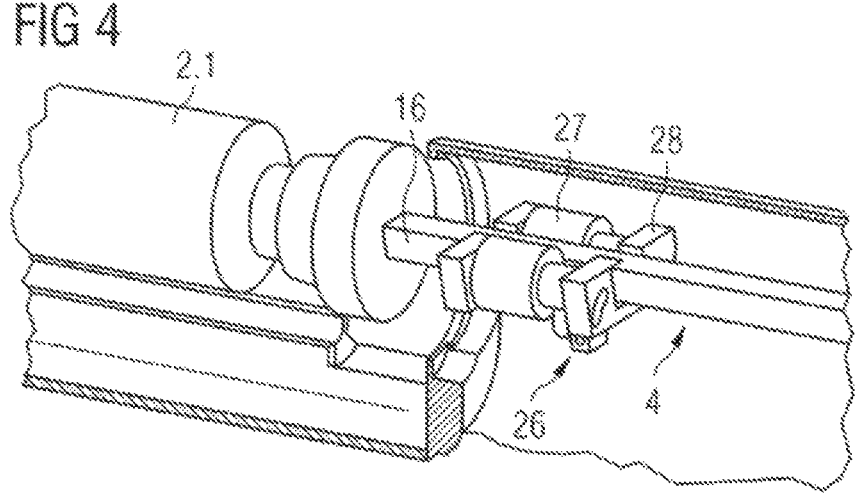

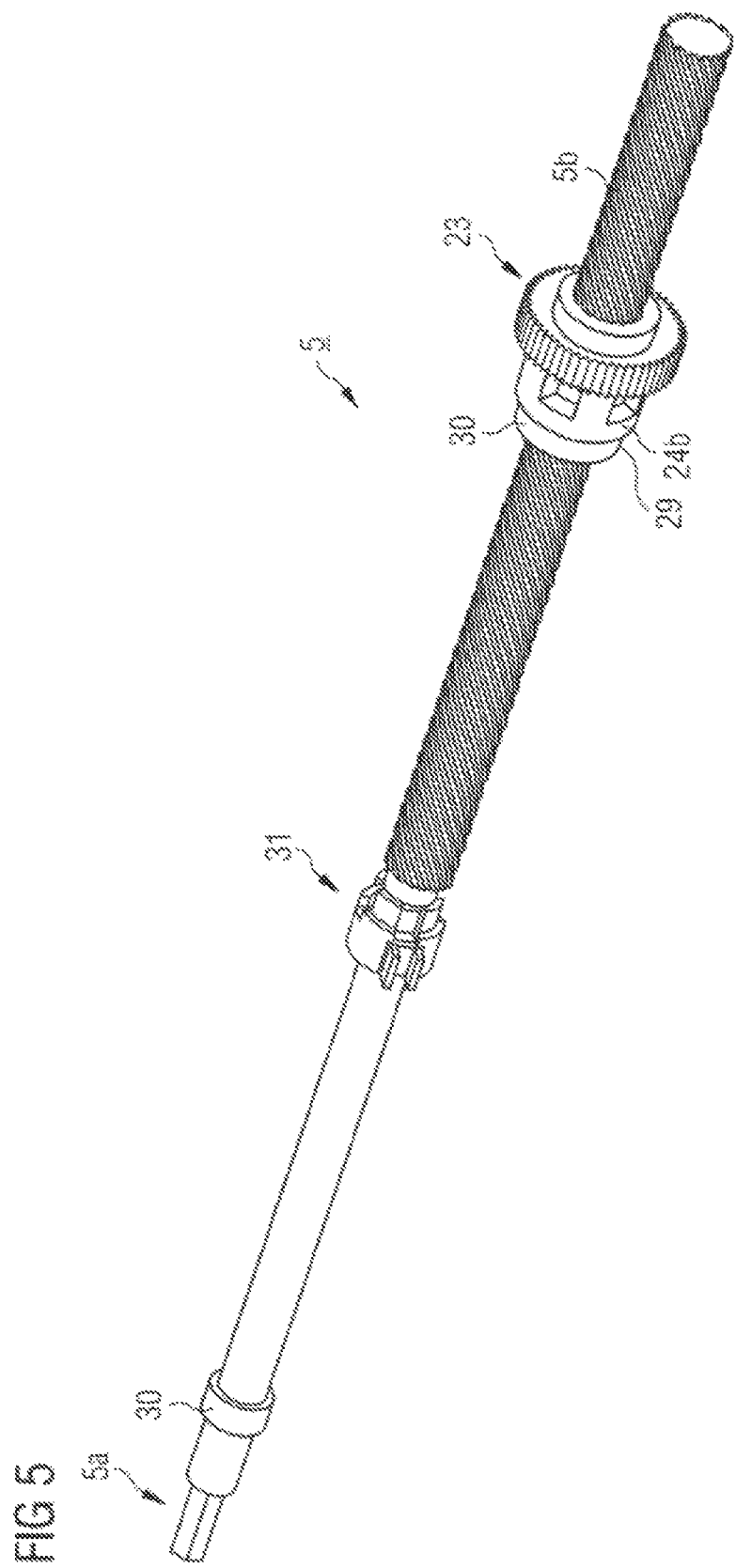

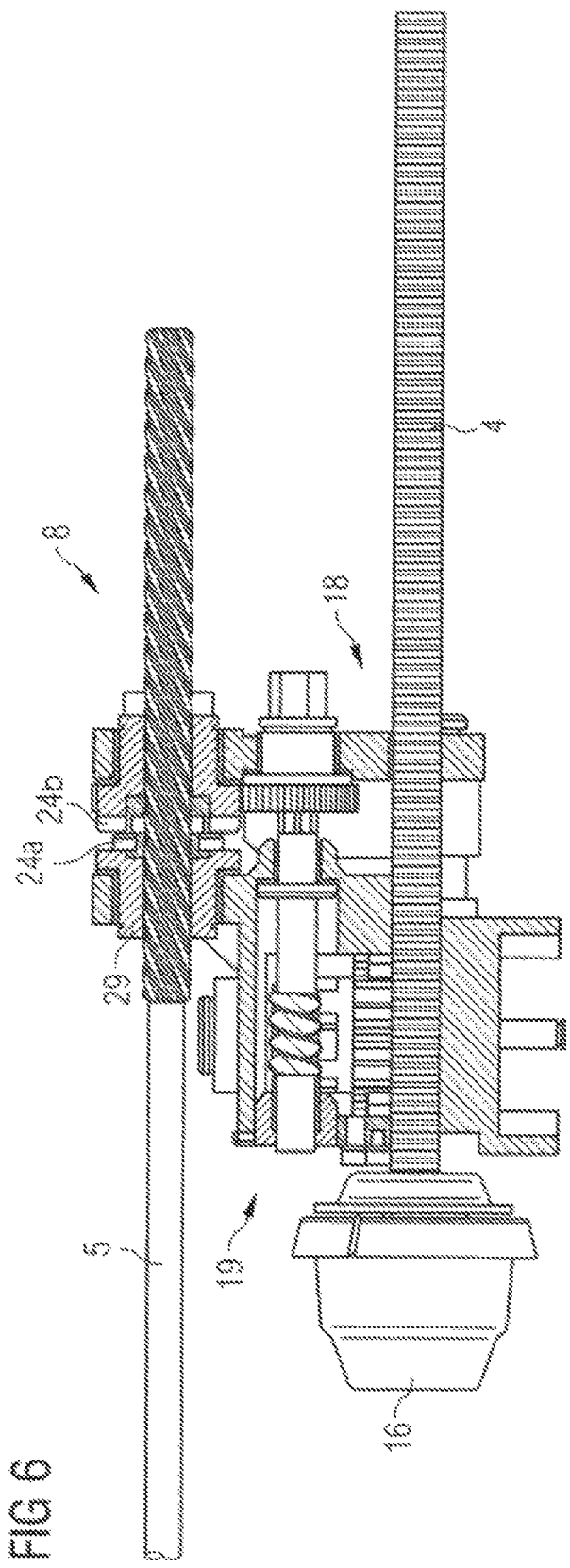

DRIVING DEVICE OF A METERING AND MIXING APPARATUS

RELATED APPLICATION(S)

This application claims priority as a continuation application under 35 U.S.C. §120 to PCT/EP2012/075155, which was filed as an International Application on Dec. 12, 2012, designating the U.S., and which claims priority to European Application 11194942.6 filed in Europe on Dec. 21, 2011. The entire contents of these applications are hereby incorporated by reference in their entireties.

FIELD

The disclosure relates to a driving device of a metering and mixing apparatus for multi-component substances, for example, multi-component adhesives, which can have at least two interconnected cartridge holders for accommodating replaceable cartridges having individual substance components, a discharge device for simultaneously discharging the substance components from the cartridges through component outlets by discharging pistons that plunge into the cartridge holder, wherein at least one discharging piston has a threading which by rotating can create a forward drive of this discharging piston, and which can have a mixing apparatus which can be connected to the component outlets and mix the discharged substance components and dispense them in a mixed state.

BACKGROUND INFORMATION

A metering and mixing apparatus is disclosed in European Patent Application 10 196 972.3 of the applicant.

A metering and mixing apparatus for mixing a dental impression compound is disclosed in DE 3 233 366 A1. This device includes a stirring unit, designed as a disposable part, with a base body that has a mixing chamber, several feed channels opening separately into the mixing chamber for the components of the impression compound, and an outlet opening for the mixed impression compound. The stirring unit also has a stirrer arranged rotatably in the mixing chamber, which can be driven by the driving device against which the stirring unit is held removably. The components of the impression compound can be held in reservoir cylinders and can be forced by pistons into the mixing chamber, and after mixing can be forced out through the outlet opening into the impression tray. The speed of advance of the actuating drives of the pistons can be varied so that both the ratio of the piston advance speed, which determines the setting time of the impression compound and the overall advance or the duration of advance and thus the quantity of impression compound can be controlled.

Reference is also made to EP 0 057 465 A2, WO 2011/025831 A1, US 2009/039113 A1, WO 2008/076941 A1 and EP 2 279 379 A1.

SUMMARY

A driving device of a metering and mixing apparatus for multi-component substances is disclosed, the driving device comprising: at least two cartridge holders configured to accommodate replaceable cartridges with individual substance components; a discharging device configured to simultaneous discharge the substance components from the cartridges through component outlets with aid of discharging pistons for entering the cartridge holders or cartridges; a mixing apparatus connected to the component outlets, for mixing discharged substance components and discharging them in mixed form; and a transmission unit for connection of a drive motor, wherein the transmission unit includes: a detector configured to detect at least a reaction pressure when such a reaction pressure builds up during discharging of at least one of the substance components, a detection signal being generated upon the reaction pressure reaching a first preset pressure value and/or dropping below a second preset pressure value, and a controller, wherein an input of the controller is connected to the detector for realizing a drive control function in response to a detection result, the transmission unit having a movable assembly which will move under influence of the reaction pressure built up during discharging of the substance component that generates the reaction pressure in a detection area of the detector.

BRIEF DESCRIPTION OF THE DRAWINGS

In the following, features disclosed herein will be described in greater detail by way of preferred exemplary embodiments with reference to the accompanying drawings, in which:

FIGS. 3A and 3B are perspective views of an exemplary embodiment of gearing component serving to drive the gear rack;

FIG. 4 is a schematic diagram in the form of a perspective view of an exemplary drive of the gear rack;

FIG. 5 is a perspective view of an exemplary embodiment of the second discharging rod of the application device according to FIG. 1;

FIG. 6 is a cutaway view of an exemplary embodiment of the transmission unit of the application device according to FIG. 1;

DETAILED DESCRIPTION

Figure 1:
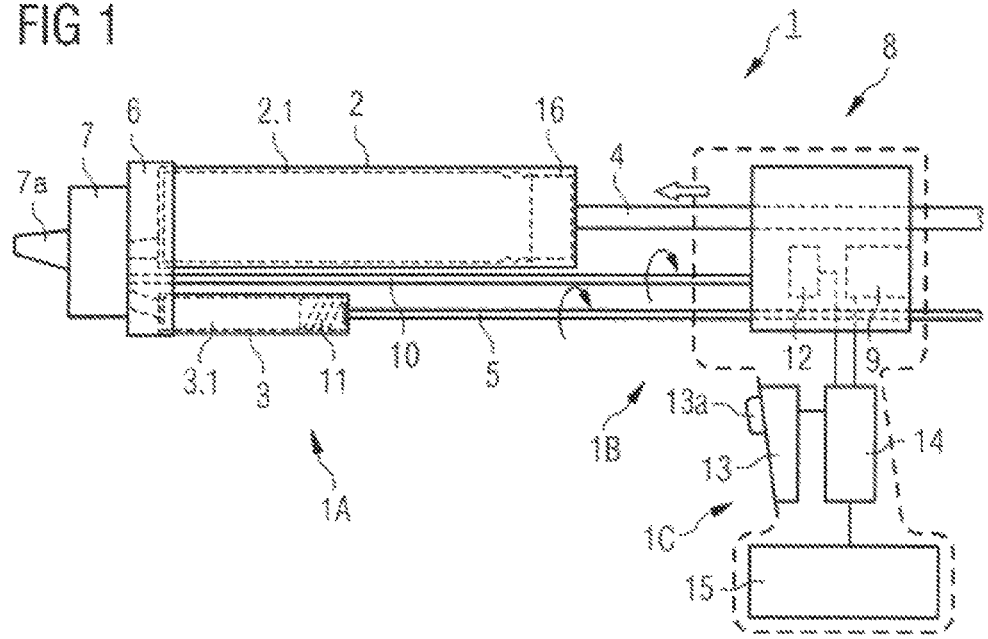
FIG. 1 is a side view of an exemplary application device according to the disclosure for a 2-component adhesive.

A driving device for a dispensing and mixing apparatus for multi-component substances is disclosed, for example, for multi-component adhesives, which can have at least two interconnected cartridge holders for accommodating replaceable cartridges having individual substance components, a discharge device for simultaneously discharging the substance components from the cartridges through component outlets by means of discharging pistons that plunge into the cartridge holder, wherein at least one discharging piston has a threading which by rotating can create a forward drive of this discharging piston, and can have a mixing apparatus which can be connected to the component outlets and mixes the discharged substance components and dispenses them in the mixed state.

The disclosure includes the driving of a metering and mixing apparatus of the aforementioned type under operating conditions such that unintended discharging of components of the multicomponent system can be blocked. At the same time, the driving device can respond to switching and control processes initiated by the operator and can make the components available. The disclosure includes supplying a detection means (e.g., a detector device) for direct or indirect detection of the counter-pressure that can build up during discharging of at least one of the substance components. The driving device can also include a control means (e.g., controller device formed by hardware and/or software) connected on the inlet side to the detection means, for a drive function that can depend on the result of the detection.

In an exemplary embodiment of the disclosure, the detection means can have a mechanical sensor or can be designed as such. Other physical action principles can be used for direct or indirect detection of the counter-pressure produced by one of the components to be discharged. For example, the detection means can have a sensor operating, which can be configured to operate based on optical, electrical or magnetic principles, for example, such as a photoelectric sensor component, a piezo sensor, a Hall sensor.

In an exemplary embodiment, the control means can have a switch, and for example, a combined detection and control means can have a microswitch, which can be achieved in a relatively cost-effective way.

In an exemplary embodiment, the drive unit includes an assembly that under the action of the reaction pressure that can build up during discharging of the substance component A moves in such a manner that upon reaching a first, preset pressure value and/or upon dropping below a second preset pressure value a detection signal can be generated. A direct detection of the relevant quantity can take place over a position shift of part of the drive device accomplished in this way. A combination of the two above-mentioned embodiments can relatively assure that the movable assembly of the drive unit and the microswitch can be attached in such a way that the assembly can move under the effect of the reaction pressure relative to an installation site of the microswitch, and upon reaching a first preset movement amount or dropping below a second preset movement amount, a switching signal can be generated.

In an exemplary embodiment of this principle of indirect detection, the movable assembly can have a counter-pressure spring element, which can supply a reaction pressure opposed to the counter-pressure during discharging of the component to establish the first and second pressure value, and thus a suitable correlation between the reaction pressure and displacement quantities. The counter-pressure spring element can substantially guarantee appropriate conversion of the primary measured quantity (reaction pressure) into the actually detected measured value (displacement), and can be a reliable restoring function.

In an exemplary embodiment, the movable assembly of the gearing can include a pressure spring element to supply an adjusting pressure force parallel to the reaction pressure during discharging of the component for fine adjustment of the preset first and/or second pressure value. These means for fine adjustment of the working point systematically follow the use of mechanical detection without any signal conversions.

In an exemplary embodiment of the drive device, the transmission unit can be designed for axial drive of a first discharging piston for discharging a substance component A driven via a first discharging rod and for rotary drive of a second discharging piston provided with threading and driven over a second spindle-like discharging rod for discharging a substance component B. In accordance with an exemplary embodiment, the movable assembly can be coupled with the first drive rod in normal operation.

In an exemplary embodiment, a switchable coupling device can be provided, which can connect the second discharging rod with the drive motor when the movable gearing housing has advanced by a certain amount under the counter-pressure.

For example, the switchable coupling device can have a first coupling element which can be essentially fixed in the axial direction with reference to the drive motor and can have a second coupling element which can be positioned in the axial direction essentially fixed relative to the movable assembly in such a manner that the second coupling element moves under the reaction pressure together with the assembly and during its movement, it engages with the coupling element.

In an exemplary embodiment, the switch of the control means can be designed such that by cooperating with a manual on/off switch of the drive device, depending on its position, the switch can establish a direction of rotation of the connected drive engine (forward or reverse drive). In an exemplary embodiment, the control means can include a delay element that can achieve delayed actuation of the drive control function in response to the detection result. For example, combining the two last-mentioned aspects can be reasonably achieved in that the control means can be designed so that the delay element brings about delayed switching of the direction of rotation in response to the detection result.

In an exemplary embodiment, to further refine the control sequences and increase the ease of use of the drive device, the control means can include a current detection devices connected to the control means for detecting a motor current of a connected electric drive motor and the control means for processing the motor current detected to perform the drive control function.

In an exemplary embodiment, for an application device for multicomponent substances, for example, multicomponent adhesives, can also lie in the area of the present disclosure, the driving device can include an integrated electric drive motor and battery power supply, as well as an operating and control unit.

FIG. 1 shows a side view (schematic representation) of an application device 1 according to the disclosure, wherein a metering and mixing apparatus 1A and a corresponding drive device 1B and an apparatus body 1C can be separately designated as components.

The metering and mixing apparatus 1A includes, shown as examples, two cartridge holders 2 and 3 with different diameters and different lengths for a tubular sack 2.1 and a solid cartridge 3.1. The larger cartridge holder 2 can be actuated with an axially movable first drive piston ("linear piston") 16 that can be connected to a first driving rod (gear rack) 4 and can be advanced by this in a linear fashion into the cartridge holder 2. The cartridge holder 3, which can have a substantially smaller diameter and can also be substantially shorter than the cartridge holder 2, according to the disclosure can be actuated by a second drive piston ("rotary piston"), which on its outside can have a threading that can engage with the inner wall of the cartridge holder 3 or a cartridge 3.1 inserted therein and can generate forward drive by rotation.

The drive unit 1B can include a transmission unit 8 which can have a single drive inlet side and three different drive outlet sides. The drive outlet sides can be an outlet for the linearly advanced gear rack 4, or an outlet for a second discharging rod 5 and an outlet for a likewise rotating drive shaft 10, which can operate a rotary mixer 7. The two cartridge holders 2 and 3 on the discharge side can be connected with a cartridge coupling 6, through which the substance also present in the cartridge holders 2 and 3 can be delivered from the component outlets to the rotary mixer 7, which can be connected to the cartridge coupling 6. The design of such a rotary mixer is known. For example, the rotary mixer can have a drive tip 7a attached at the front, through which the mixed substance is ultimately discharged.

The transmission unit 8 in the embodiment of the metering and mixing apparatus 1 shown in FIG. 1 can be driven with the aid of an electric motor 9. A microswitch 12 can be provided, the function of which will be described further below. The device body 1C can include an operating unit 13 with a manually actuatable on and off switch 13a, a drive control unit 14 and a battery pack 15.

Figure 2:
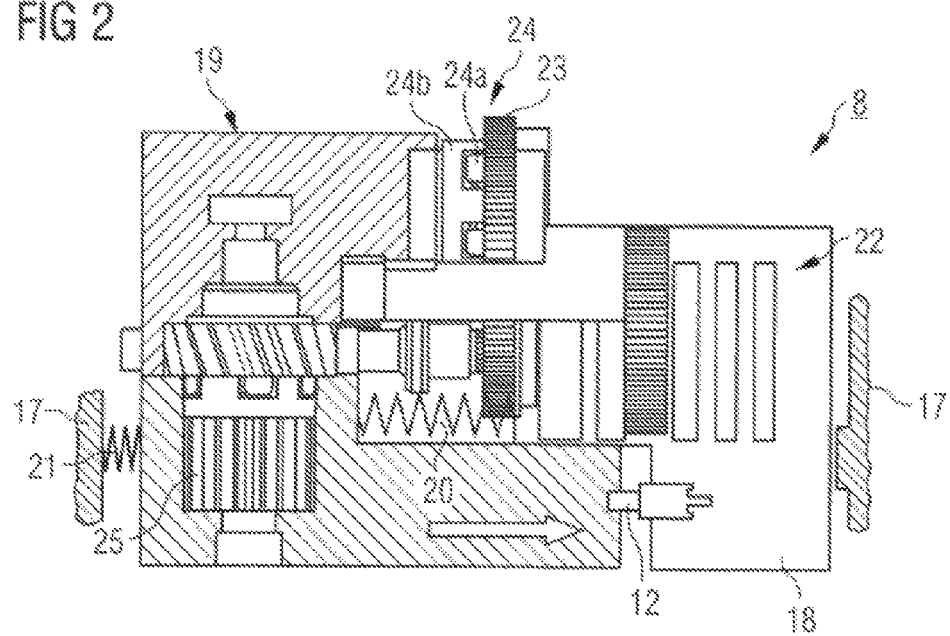
FIG. 2 is a representation of an exemplary structure of a transmission unit of the application device according to FIG. 1.

FIGS. 2 and 6 show the structure of an exemplary embodiment of the transmission unit 8. The method of presentation of FIG. 2 and additional figures differs from that in FIG. 1 in that in FIG. 2, the gearing components forming part of the gear rack 4 can be at the bottom and the components belonging to the second discharging rod 5 can be located at the top.

The transmission unit 8 can include a first assembly 18 fixed in place relative to a wall of an apparatus housing 17 of the application device and a second assembly 19 carried movably in the apparatus housing. The two gearing assemblies 18 and 19 can be clamped elastically together by means of a counter-pressure spring 20 (shown here symbolically) and the movable assembly 19 can be elastically supported against the apparatus housing 17 with an additional spring element 21, which can also be designated as a pressure spring element in the remainder of the document. The first assembly 18 can include a planetary gearing 22, which can be in contact with a drive pinion of the drive motor, and the output 23 for driving the spindle-like second drive rod and driven gears for the first discharging rod (gear rack) and the drive shaft of the mixer.

At the output for the second discharging rod, a switchable coupling (claw coupling) 24 is provided, which can include a first coupling element 24a fixed in place relative to the first assembly 28 and a second coupling element 24b fixed in place relative to the second assembly 19. A gearing component 25 can be placed in the second assembly 19 for driving the first discharging rod (gear rack), which will be described herein.

The microswitch 12 can be permanently attached to the first assembly 18, and can be positioned such that it can be actuated in a preset movement position of the second assembly 19.

The functioning of the two-part design of the transmission unit 8 with the spring supports mentioned and the microswitch is as follows in a simplified description:

In the switched-off state of the application device, the second assembly 19 can advance forward relative to the first assembly 18 of the transmission unit 8 due to the force of the counter-pressure spring 20 that the first and second coupling elements 24a, 24b of the switchable coupling 24 are not connected and the second assembly also does not touch the microswitch 12. The exact resting position of the second assembly 19 can be adjusted by suitable selection of the back-pressure spring 20 and the forward-pressure spring 21, adapted to one another, and the response behavior of the mounting of the second assembly on startup of the apparatus.

On startup the drive force can proceed from the drive motor over the planetary gearing 22 and the gearing component 25 to the gear rack 4 and can cause it to move in the drive direction of the metering and mixing apparatus (to the left in FIG. 1 and FIG. 2). As soon as the first discharging piston 16 encounters the end of the filled cartridge 2.1 facing it, a reactive pressure can build up, because of the viscosity of the substance component contained therein and can be transmitted over the gear rack 4 to its drive pinion (see FIG. 3A) and can be transmitted over its mounting to the second component 19. It can cause movement of the second assembly 19 relative to the first assembly 18 against the spring force of the counter-pressure spring 20. As soon as a certain shift amount is reached, the coupling elements 24a, 24b can engage, and the flow of force from the drive motor can reach the spindle-like second discharging rod 5, setting this into rotation and driving the self-cutting piston. At the same time, the microswitch 12 can be actuated by the movement of the second assembly 19. In accordance with an exemplary embodiment, the function connected with this process is described herein.

As a result of this design and the resulting sequence it can be relatively ensured that discharge of the component B contained in cartridge 3.1 takes place only if the component A of the multi-component system contained in cartridge 2.1 is also discharged. This is also true if a partially emptied cartridge with component A is placed in the device at point 1 and the operation is started in the fully retracted initial position of the gear rack 4. For example, this then moves forward in idle mode, and the second gearing assembly 19 remains in the outlet state shifted relative to the first assembly 18, until the first discharging piston 16 encounters the end of the partially filled cartridge. Only at this time is a reaction force built up there, which presses the second assembly 19 against the first assembly 18 and thus closes the switchable coupling 24, so that the drive force can also be introduced into the second discharging rod (spindle) 5. In this application as well, therefore, component B can only be discharged at the correct time.

FIGS. 3A and 3B show an exemplary embodiment of the gearing component serving to drive the first discharging rod (gear rack 4), a coupling-capable screw drive 25 in the coupled-in (FIG. 3A) and uncoupled (FIG. 3B) states. The screw drive can include a screw 25a with a spline shaft, which is supported in an axial bearing 25b and can be driven over a drive gear of the planetary gearing. Two worm gears 25c with helical teeth can be engaged with the screw 25a, with a claw coupling 25d associated to each of them. With the displaceable coupling element of this coupling 25d in each case a straight-toothed drive pinion 25e can be permanently connected, which in the engaged state of the coupling 25d can move along with the worm gear 25c and can transmit the drive force to the gear rack (no. 4 in FIG. 1), not shown here, with which it meshes. In the disengaged state shown in FIG. 3B the pinions 25e can essentially rotate freely, so that the gear rack supported between them and engaging with them can be moved axially practically without resistance, such that it can be easily drawn back to reload the application device with a full cartridge 2.1 (FIG. 1).

FIG. 4 is a schematic diagram in the form of a perspective view of an exemplary drive of the gear rack as shown in FIG. 1. The gear rack 4 can be driven over a spur gear gearing 26 and two screws 27, which can be pivotably supported in a guide bar 28. By pivoting this screw 27 by means of an actuating lever, its engagement with the gear rack 4 can be undone, such that the gear rack can be withdrawn without resistance. In an exemplary embodiment, the gearing part can also be provided such that the gear rack 4 that can be driven over two pinions directly meshing in the flanks thereof, with their rotational axes perpendicular to the length of the gear rack. This drive concept is familiar to those skilled in the art and therefore will not be illustrated or described in greater detail.

FIG. 5 shows a perspective view of an exemplified embodiment of the second discharging rod 5. As shown in FIG. 5, the second discharging rod 5 at its end (on the left in the figure) can have an engaging element 5a, which can be a polygon for engaging in a correspondingly-shaped engagement device on the discharging rod piston 11 (FIG. 1), which represents a separate part from the discharging rod and for example can be part of the cartridge 3.1 and can be delivered with it. The opposite end section 5b of the discharging rod 5 can have a spiral toothed system with a high flank lead, resulting in non-self-locking behavior. In this terminal section 5b the spindle-like discharging rod can engage with an inner-toothed drive gear 29 of the transmission unit corresponding to the exterior threading of section 5b, which can be permanently connected to or made in one piece with the second coupling element 24b of the switchable coupling 24 shown in FIG. 2 as described herein.

The drive rod or spindle 5 can be supported at the bearing points 30. Between the end provided with the engaging element 5a and the spiral-toothed end section 5b, the drive rod or spindle 5 can include a cylindrical axis and in this area has an entrained braking device 31 for generating a minimal braking torque (in the range of 0.5 to 1.0 Nm), which can also generate an axial advance when idling, for example, in the non-engaged state of the discharging rod with the corresponding discharging piston. The braking element 31 can also serve as a position marker for labeling the axial position of the discharging rod in the field of view of an operator or for an optical detection device or can bear such a marking element. In accordance with an exemplary embodiment, the second discharging rod (like the first discharging rod) can move forward, and thus whether correct discharging of component B is taking place. Thus, failure caused, for example, by lack of correct engagement between the discharging rod and the separate discharging piston, can be recognized relatively immediately and the occurrence of incorrect adhesion points can be suppressed.

FIG. 6 shows a sectional view of additional essential parts of the transmission unit 8 with the discharging rods 4 and 5 in place to make their position assignment clear. With regard to the screw drive 25' for driving the first discharging rod 4, the construction can be modified versus the gearing component 25 sketched in FIG. 2 as well as FIGS. 3A and 3B.

Figure 7A:
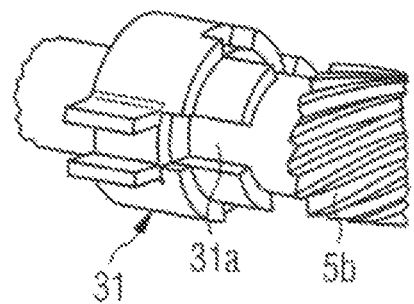
FIGS. 7A and 7B are schematic diagrams in the form of perspective views of an exemplary discharging rod according to FIG. 5.
Figure 7B:
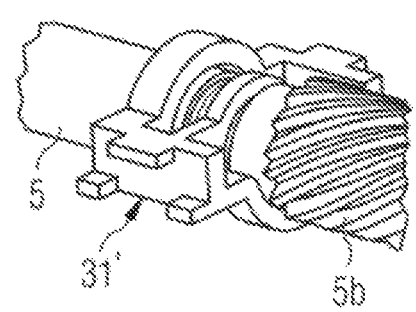

FIGS. 7A and 7B shows further details of the braking element 31 illustrated in FIG. 5, which can be an entrained wrap spring housing, and the wrap spring 31a can also be visible. FIG. 7B shows an exemplary embodiment of the braking element as an entrained plastic brake 31'. Both brake element designs are known to those skilled in the art and therefore will not be explained further.

Figure 8:
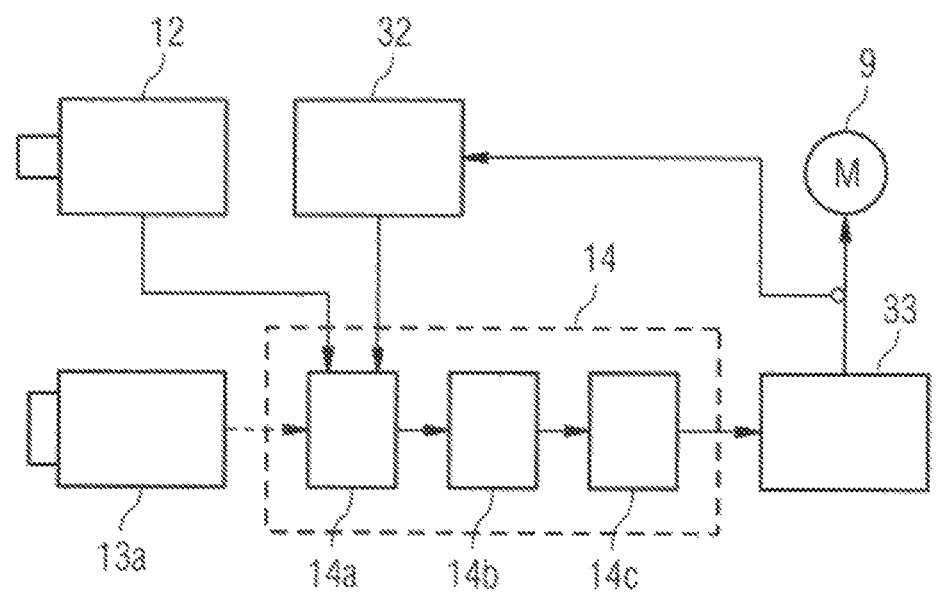
FIG. 8 is a block diagram of an exemplary embodiment of a sensor that forms part of the drive device 1B of the application apparatus according to FIG. 1.

FIG. 8 shows schematically on a block diagram the structure of a sensor system and the associated control means of the proposed drive device. The sensor system, in addition to the previously-mentioned microswitch 12, can include on the on/off switch ("trigger") 13a, serving as the primary operating element, or in addition to this or as a sensory replacement for it, and a current detection unit 32 for detecting the motor current of the drive motor 9, which can be supplied to this over a motor control 33. The drive control unit 14 can include a sensor signal processing step 14a, a delay element 14b and a control signal outlet step 14c.

A processing algorithm can be implemented in the sensor signal processing unit 14a, the signals from the microswitch 12, which can contain information on the discharge of component A, can be placed in an appropriate relationship to data originating from the on/off switch 13a or the current detection unit 32 and can provide information on the operating state of the motor. The processing result can also be subjected to an appropriate chronological evaluation (likewise on the basis of stored algorithms) in the delay element 14b, and as a result, a suitable motor control signal can be emitted in operating situations of the application device by the control signal output unit 14c.

Figure 9A:
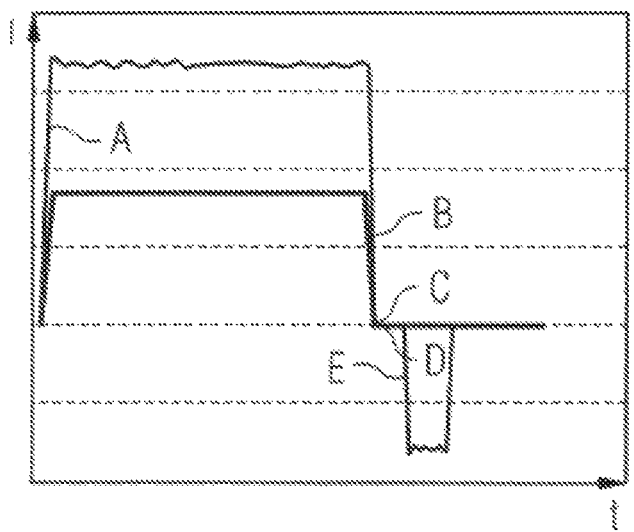
FIGS. 9A and 9B are exemplary motor current-time diagrams for exemplary embodiments of a control sequence of the drive control.
Figure 9B:
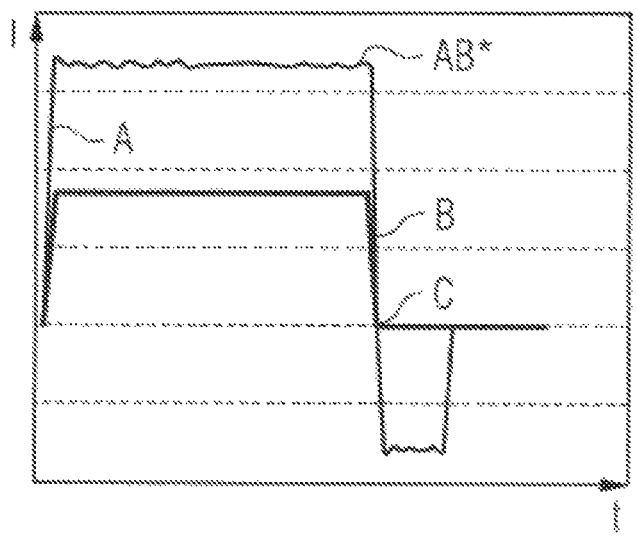

FIGS. 9A and 9B show time sequences based on motor current-time diagrams, which each start at a point A with an increase in the detected motor current I based on a turning-on action of the on/off switch 13a. At point B in FIG. 9A an on/off switch can be slowly released; at point C the flow detection unit 32 can detect a motor current value of 0, after which, during a brief phase D, the sensor signal processing unit 14a can test whether the motor current remains at the value of 0 to determine whether the on/off switch was released deliberately or accidentally. If the former is the case, then at point E the signal from the still-depressed microswitch 12 can be processed, such that control signal output unit 14c can emits a signal that causes a return stroke of the motor 9.

FIG. 9B shows an alternative version of a comparable control sequence. Here in the sensor signal processing unit 14a before time B (release of the on/off switch) in a phase AB* the motor current value is detected and stored and used for comparison with the current value measured at time point C. Here the processing unit recognizes, based on the comparison result, whether the on/off switch was deliberately released, and as long as a corresponding signal is available from the microswitch 12, starts the motor return stroke at practically the same time.

With the procedure described in both variants, an unnecessary return stroke of the motor in case of accidental or very brief release of the trigger can be prevented, but at the same time a return stroke that is appropriate because of deliberate termination of the drive process can be initiated, so that an "overshooting" discharge of multi-component substances, for example, component A (which would still be under drive pressure if the motor were simply turned off) can be suppressed. At the same time, with the (slight) return stroke and with the end of effect of the reaction force coming from component A the second gearing assembly 19 is made to return to its initial position at a maximum distance from the first assembly 18, thus releasing the coupling 24 and the microswitch 12. This can be a suitable shutoff and non-use state of the application device.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A driving device of a metering and mixing apparatus for multi-component substances, the driving device comprising:
   at least two cartridge holders configured to accommodate replaceable cartridges with individual substance components;
   a discharging device configured to simultaneous discharge the substance components from the cartridges through component outlets with aid of discharging pistons for entering the cartridge holders or cartridges;

a mixing apparatus connected to the component outlets, for mixing discharged substance components and discharging them in mixed form; and a transmission unit for connection of a drive motor, wherein the transmission unit includes:

a detector configured to detect at least a reaction pressure when such a reaction pressure builds up during discharging of at least one of the substance components, a controller configured to have an input connected to the detector for realizing a drive control function in response to a detection result; and a movable assembly configured to move under influence of the reaction pressure built up during discharging of the substance component that generates the reaction pressure in a detection area of the detector, wherein the transmission unit is configured to generate a detection signal based on movement of the movable assembly when at least one of the reaction pressure reaches a first preset pressure value and the reaction pressure drops below a second preset pressure value.

2. The driving device according to claim 1, comprising: a mechanical pickup on the detector.

3. The driving device according to claim 1, wherein the detector has a pickup operating on an optical, electrical or magnetic basis.

4. The driving device according to claim 3, wherein pickup comprises:

a photoelectric cell, a piezoelectric pickup, or a Hall sensor.

5. The driving device according to claim 1, wherein the controller has a switch.

6. The driving device according to claim 1, wherein the detector and the controller are configured as a combined detector and controller having a microswitch.

7. The driving device according to claim 6, comprising:

a signal generator for generating a switching signal upon reaching a first preset movement amount or dropping below a second preset movement amount; and wherein the movable assembly of the transmission unit and the microswitch are attached such that the assembly will move under action of the reaction pressure relative to an installation point of the microswitch.

8. The driving device according to claim 1, wherein the movable assembly comprises:

a counter-pressure spring element for supplying a counter-pressure force opposing the reaction pressure during discharging of the component, to establish the first and second preset pressure values.

9. The driving device according to claim 8, wherein the movable assembly of the transmission unit comprises:

a pressure spring element for supplying an adjusting pressure force parallel to the reaction pressure during discharging of the component, for fine adjustment of the first and/or second preset pressure values.

10. The driving device according to claim 1, wherein the transmission unit comprises:

an axial drive of a first discharging piston driven over a first discharging rod for discharging a first substance component and for rotary drive of a threaded second discharging piston driven over a second, spindle-like discharging rod for discharging a second substance component, and wherein the movable assembly is coupled with the first discharging rod.

11. The driving device according to claim 10, comprising:

a switchable coupling device, which connects the second drive rod with the drive motor when the movable assembly has advanced by a preset amount under the reaction pressure.

12. The driving device according to claim 11, wherein the switchable coupling device comprises:

a first coupling element which is essentially fixed in the axial direction relative to the drive motor; and a second coupling element which is essentially fixed in the axial direction relative to the movable assembly, such that under the reaction pressure, the second coupling element will move together with the assembly and upon its displacement, engage with the first coupling element.

13. The driving device according to claim 5, wherein the switch of the controller is configured to interact with a manual on/off switch of the driving device, the switch being configured to establish a direction of rotation of the connected drive motor.

14. The driving device according to claim 1, wherein the controller comprises:

a delay element for delayed triggering of the driving control function in response to the detection signal.

15. The driving device according to claim 14, wherein the delay element is configured for a delayed switching over of a direction of rotation of the drive motor in response to the detection signal from the detector.

16. The driving device according to claim 1, wherein the controller comprises:

a current detector for detecting a motor current of the drive motor, the controller processing detected motor current to perform the drive control function.

17. The driving device according to claim 1, in combination with one or more replaceable cartridges with individual substance components.

18. The driving device according to claim 1, wherein the drive motor is an integrated electric drive motor.

19. The driving device according to claim 18, comprising:

a battery power supply.

* * * * *